United States Patent [19]

Sugano et al.

[11] Patent Number: 5,510,502

[45] Date of Patent: Apr. 23, 1996

[54] CATALYST COMPONENT FOR USE IN THE POLYMERIZATION OF α-OLEFINS AND PROCESS FOR PRODUCING α-OLEFIN POLYMERS USING THE SAME

[75] Inventors: Toshihiko Sugano; Tomohiko Takahama, both of Yokkaichi, Japan

[73] Assignee: Mitsubishi Chemical Corporation, Tokyo, Japan

[21] Appl. No.: 198,257

[22] Filed: Feb. 18, 1994

[30] Foreign Application Priority Data

Feb. 19, 1993 [JP] Japan .................................. 5-030748

[51] Int. Cl.$^6$ .............................. C07F 17/00; C07F 7/28; C07F 9/00; C07F 11/00
[52] U.S. Cl. ................... 556/11; 556/12; 556/28; 556/43; 556/53; 556/58; 502/117; 502/103; 526/160
[58] Field of Search ................... 556/11, 12, 28, 556/43, 53, 58; 502/103, 117

[56] References Cited

U.S. PATENT DOCUMENTS

| | | | |
|---|---|---|---|
| 5,120,867 | 6/1992 | Welborn, Jr. ............................. | 556/12 |
| 5,145,819 | 9/1992 | Winter et al. ........................... | 502/117 |

FOREIGN PATENT DOCUMENTS

| | | |
|---|---|---|
| 0372414 | 6/1990 | European Pat. Off. . |
| 0490256 | 6/1992 | European Pat. Off. . |
| 0496193 | 7/1992 | European Pat. Off. . |
| 0529908 | 3/1993 | European Pat. Off. . |

*Primary Examiner*—Porfirio Nazario-Gonzales
*Attorney, Agent, or Firm*—Oblon, Spivak, McClelland, Maier, & Neustadt

[57] ABSTRACT

A catalyst component for use in the polymerization of α-olefins, comprising a compound represented by the following general formula [I]:

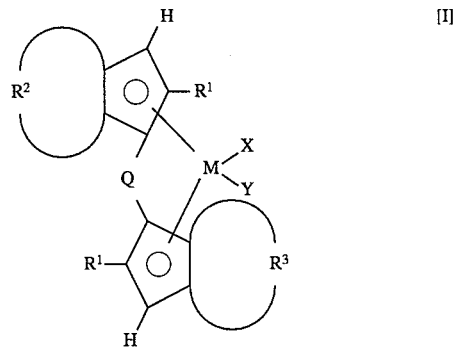

wherein $R^1$s represent a hydrogen atom, a $C_{1-6}$ hydrocarbon group or a $C_{1-12}$ hydrocarbon group containing silicon; each of $R^2$ and $R^3$ which forms the condensed ring represents a divalent $C_{3-20}$ saturated or unsaturated hydrocarbon group, provided that at least one of $R^2$ and $R^3$ forms a ring condensed with the cyclopentadiene which is a seven- to twelve-membered ring having an unsaturated bond inherent in $R^2$ or $R^3$; Q represents a $C_{1-20}$ divalent hydrocarbon group, a silylene group, a silylene group with a $C_{1-20}$ hydrocarbon group, a germylene group, or a germylene group with a $C_{1-20}$ hydrocarbon group; X and Y represent H, a halogen, a $C_{1-20}$ hydrocarbon group, or a $C_{1-20}$ hydrocarbon group containing oxygen, nitrogen or phosphorus; and M represents a Group IVB to VIB transition metal of the Periodic Table. Production of α-olefin polymers having a high melting point and a high molecular weight in a high yield and a process for producing α-olefin polymers is made possible upon the use of the catalyst.

8 Claims, No Drawings

CATALYST COMPONENT FOR USE IN THE POLYMERIZATION OF α-OLEFINS AND PROCESS FOR PRODUCING α-OLEFIN POLYMERS USING THE SAME

BACKGROUND OF THE INVENTION

1. Field of the Invention

The present invention relates to a catalyst component for use in the polymerization of α-olefins. More specifically, the present invention relates to a catalyst component, which makes possible the production of α-olefin polymers having a high melting point, a catalyst for the polymerization of α-olefins using said catalyst component, and a process for producing α-olefin polymers using said catalyst.

2. Related Art

A so-called Kaminsky catalyst has been well known as a homogeneous catalyst for the polymerization of olefins. This catalyst is characterized in that it has a very high catalytic activity for the polymerization and can provide a polymer with a narrow molecular weight distribution.

As transition metal compounds useful for the production of isotactic polyolefins by Kaminsky catalyst, ethylenebis(indenyl)zirconium dichloride and ethylenebis(4,5,6,7-tetrahydroindenyl)zirconium dichloride (Japanese Patent Laid-Open Publication No. 130314/1986) have been known. They, however, have disadvantages including that the resultant polyolefins have a low molecular weight and polymerization at a low temperature can provide high-molecular weight polyolefins only at the sacrifice of the polymerization activity of the catalyst. Further, it has been known that a high-molecular weight polymer can be produced when a hafnium compound is used instead of zirconium as a transition metal compound (Journal of Molecular Catalysis, 56 (1989) p. 237–247). However, this method may, to the best of our knowledge, have a shortcoming in that the polymerization activity is low.

Furthermore, dimethylsilylbis-substituted cyclopentadienylzirconium dichloride and the like are proposed in Japanese Patent Laid-Open Publication No. 301704/1989, Polymer Preprints, Japan Vol. 39, No. 6, p. 1614–1616 (1990) and Japanese Patent Laid-Open Publication No. 12406/1991, and dimethylsilylenebis(indenyl)zirconium dichloride and the like are proposed in Japanese Patent Laid-Open Publication Nos. 295007/1988 and 275609/1989. These proposals may have made possible the production of polymers having a high stereoregularity and a high melting point by polymerization at relatively low temperatures. To the best of our knowledge, however, a lowering in the stereoregularity, melting point and molecular weight of the polymers would be significant when the polymerization is carried out under high temperature conditions that are favorable from the viewpoint of economy.

Japanese Patent Laid-Open Publication Nos. 268307/1992 and 268308/1992 suggest that the stereoregularity and molecular weight can be improved to some extent when use is made of cyclopentadienyl compounds as referred to above which have a substituent to the position (2-position) adjacent to the crosslinking group in the cyclopentadienyl compounds. This method, however, would still be unsatisfactory in the performance under polymerization conditions of an increased polymerization temperature regarded as advantageous from the viewpoint of economy.

An object of the present invention is to provide a catalyst component for the polymerization of α-olefins, by which catalyst extrudable and injection-moldable olefin polymers having a high molecular weight and a high melting point can be obtained in a high yield, a catalyst for the polymerization of α-olefins and a process for producing α-olefin polymers.

SUMMARY OF THE INVENTION

The present invention has been made as a result of studies with a view to solving the above-described problem.

More specifically, the present invention provides a component of a catalyst for the polymerization of α-olefins which comprises a compound represented by the following general formula [I]:

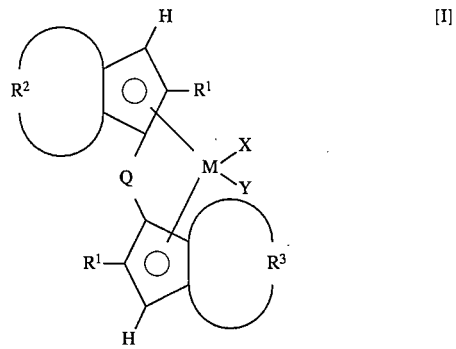

wherein $R^1$s each independently represent a hydrogen atom, a hydrocarbon group having 1 to 6 carbon atoms or a hydrocarbon group having 1 to 12 carbon atoms with a silicon atom contained therein; each of $R^2$ and $R^3$ independently represents a divalent saturated or unsaturated hydrocarbon group having 3 to 20 carbon atoms which forms a ring condensed with the five-membered ring to which it is attached, provided that at least one of $R^2$ and $R^3$ forms the ring condensed which is a seven- to twelve-membered ring having an unsaturated bond inherent in $R^2$ or $R^3$ used; Q represents a divalent hydrocarbon group having 1 to 20 carbon atoms, a silylene group, a silylene group with a hydrocarbon group having 1 to 20 carbon atoms, a germylene group, or a germylene group with a hydrocarbon group having 1 to 20 carbon atoms, which group combines the two five-membered rings with each other; X and Y each independently represent a hydrogen atom, a halogen atom, a hydrocarbon group having 1 to 20 carbon atoms, or a hydrocarbon group having 1 to 20 carbon atoms with an oxygen atom, a nitrogen atom, a silicon atom or a phosphorus atom contained therein; and M represents a Group IVB to VIB transition metal of the Periodic Table.

Further, the present invention relates to a catalyst for the polymerization of α-olefins, comprising the above-described catalyst component.

More specifically, the catalyst for the polymerization of α-olefins according to the present invention comprises in combination:

Component (A) which is a catalyst component for the polymerization of α-olefins, comprising a compound represented by the following general formula [I]:

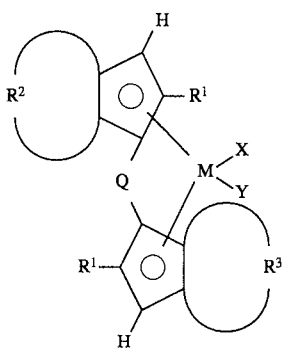

wherein $R^1$s each independently represent a hydrogen atom, a hydrocarbon group having 1 to 6 carbon atoms or a hydrocarbon group having 1 to 12 carbon atoms with a silicon atom contained therein; each of $R^2$ and $R^3$ independently represents a divalent saturated or unsaturated hydrocarbon group having 3 to 20 carbon atoms which forms a ring condensed with the five-membered ring to which it is attached, provided that at least one of $R^2$ and $R^3$ forms the ring condensed which is a seven- to twelve-membered ring having an unsaturated bond inherent in $R^2$ or $R^3$ used; Q represents a divalent hydrocarbon group having 1 to 20 carbon atoms, a silylene group, a silylene group with a hydrocarbon group having 1 to 20 carbon atoms, a germylene group, or a germylene group with a hydrocarbon group having 1 to 20 carbon atoms, which group combines the two five-membered rings with each other; X and Y each independently represent a hydrogen atom, a halogen atom, a hydrocarbon group having 1 to 20 carbon atoms, or a hydrocarbon group having 1 to 20 carbon atoms with an oxygen atom, a nitrogen atom, a silicon atom or a phosphorus atom contained therein; and M represents a Group IVB to VIB transition metal of the Periodic Table; and Component (B): (i) an aluminum oxy compound, (ii) a Lewis acid or (iii) an ionic compound which can react with Component (A) to convert Component (A) to a cation.

Further, the present invention relates to a process for producing an α-olefin polymer wherein use is made of the above-described catalyst.

More specifically, the process for producing an α-olefin polymer according to the present invention comprises contacting an α-olefin with a catalyst comprising in combination:

Component (A) which is compound of a catalyst component for the polymerization of α-olefins, comprising a compound represented by the following general formula [I]:

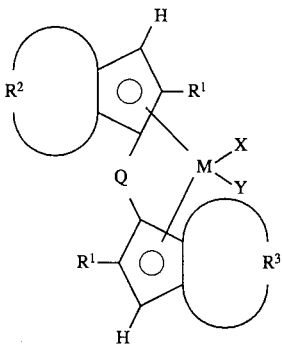

wherein $R^1$s each independently represent a hydrogen atom, a hydrocarbon group having 1 to 6 carbon atoms or a hydrocarbon group having 1 to 12 carbon atoms with a silicon atom contained therein; each of $R^2$ and $R^3$ independently represents a divalent saturated or unsaturated hydrocarbon group having 3 to 20 carbon atoms which forms a ring condensed with the five-membered ring to which it is attached, provided that at least one of $R^2$ and $R^3$ forms the ring condensed which is a seven- to twelve-membered ring having an unsaturated bond inherent in $R^2$ or $R^3$ used; Q represents a divalent hydrocarbon group having 1 to 20 carbon atoms, a silylene group, a silylene group with a hydrocarbon group having 1 to 20 carbon atoms, a germylene group, or a germylene group with a hydrocarbon group having 1 to 20 carbon atoms, which group combines the two five-membered rings with each other; X and Y each independently represent a hydrogen atom, a halogen atom, a hydrocarbon group having 1 to 20 carbon atoms, or a hydrocarbon group having 1 to 20 carbon atoms with an oxygen atom, a nitrogen atom, a silicon atom or a phosphorus atom contained therein; and M represents a Group IVB to VIB transition metal of the Periodic Table; and Component (B) which is (i) an aluminum oxy compound, (ii) a Lewis acid or (iii) an ionic compound which can react with Component (A) to convert Component (A) to a cation.

By the use of the catalyst according to the present invention, the production of α-olefin polymers having a high melting point and a high molecular weight in a high yield becomes possible.

The mechanism through which the effect or advantage inherent in the present invention are developed has not been elucidated yet, but it is believed to be as follows although it is to be noted that the present invention is not bound by the following mechanism. From a comparison of the compound of the present invention with the conventional metallocene compound having a condensed ring formed adjacent to a five-membered ring, such as indenyl group, it is expected that the difference of the compound [I] in the present invention from the conventional compound in terms of the positional relationship between the condensed ring and the five-membered ring with which the condensed ring is condensed, specifically in terms of the positional relationship between the condensed ring and the metal M coordinated to the five-membered ring, or more specifically, the difference of the compound [I] in the present invention in terms of the positional relationship between the carbon atom adjacent to the 4-position of the condensed ring on the 4- and 5-positions of the five-membered ring (the bonding site of the crosslinking group Q on the five-membered ring being defined as the 1-position, and the bonding site of the substituent $R^1$ as the 2-position), and the five-membered carbon ring or more specifically, the metal M coordinated to the five-membered ring, is such that a better steric hindrance effect can be attained when the condensed ring is a seven- to twelve-membered ring, which contributes to an improvement in the stereoregularity of the resultant polymer. Further, the presence of the double bond within the condensed seven- to twelve-membered ring too has a favorable effect. Specifically, when the polymerization is carried out at relatively high temperature conditions regarded as advantageous from the viewpoint of economy since higher yield is obtainable, the use of a compound not having a double bond within the ring, such as a 4,5,6,7-tetrahydroindenyl group, gives rise to a remarkable deterioration in stereoregularity and lowering of the molecular weight, whereas this unfavorable phenomenon is not observed when use is made of the compound of the present invention. The reason for this is believed to be that the double bond present in the seven- to twelve-membered ring composed of $R^2$ or $R^3$ inhibits the movement of the site adjacent to the 4-position which causes the steric hindrance, so that the structure of the ligand becomes so firm that the lowering of the stereoregularity and molecular weight is reduced even when the polymerization temperature is high.

The above-described effect is considered unexpectable from the conventional techniques,

DETAILED DESCRIPTION OF THE PREFERRED EMBODIMENTS OF THE INVENTION

The present invention relates to a polymerization catalyst component, which comprises a compound which is described below as Component (A). The present invention relates further to a catalyst for the polymerization of α-olefins, which comprises Component (A) and Component (B) which will be described in more detail, and still further to a process for producing an α-olefin polymer, which comprises contacting an α-olefin with a catalyst comprising this catalyst. The expressions "comprises" herein is intended to mean that the given specified compounds or components or steps can be used in combination with other compounds or components or steps as long as the additional compounds and components are not detrimental to the effect of the present invention.

<Component (A)>

The catalyst component (A) of the present invention comprises a transition metal compound represented by the following general formula [I]:

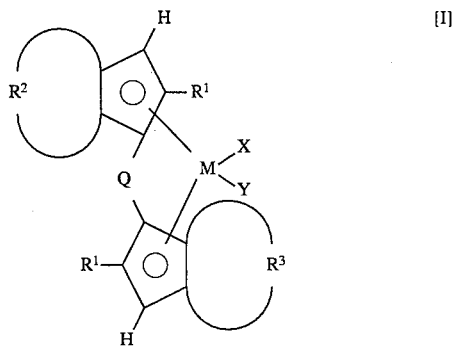

wherein $R^1$s each independently represent a hydrogen atom, a hydrocarbon group having 1 to 6 carbon atoms or a hydrocarbon group having 1 to 12 carbon atoms with a silicon atom contained therein; each of $R^2$ and $R^3$ independently represents a divalent saturated or unsaturated hydrocarbon group having 3 to 20 carbon atoms which forms a ring condensed with the five-membered ring to which it is attached, provided that at least one of $R^2$ and $R^3$ forms the ring condensed which is a seven- to twelve-membered ring having an unsaturated bond inherent in $R^2$ or $R^3$ used; Q represents a divalent hydrocarbon group having 1 to 20 carbon atoms, a silylene group, a silylene group with a hydrocarbon group having 1 to 20 carbon atoms, a germylene group, or a germylene group with a hydrocarbon group having 1 to 20 carbon atoms, which group combines the two five-membered rings with each other; X and Y each independently represent a hydrogen atom, a halogen atom, a hydrocarbon group having 1 to 20 carbon atoms, or a hydrocarbon group having 1 to 20 carbon atoms with an oxygen atom, a nitrogen atom, a silicon atom or a phosphorus atom contained therein; and M represents a Group IVB to VIB transition metal of the Periodic Table.

The metallocene compound represented by formula [I] used in the present invention has a significant feature in that two five-membered cyclic ligands having the substituents $R^1$, $R^2$ and $R^3$ are asymmetric about a plane containing M, X and Y when viewed from their relative position in terms of the group Q.

As described above, $R^1$ is a hydrogen atom, a hydrocarbon group having 1 to 6 carbon atoms or a hydrocarbon group having 1 to 12 carbon atoms with a silicon atom contained therein. More specifically, $R^1$ is a hydrogen atom, a saturated hydrocarbon group such as alkyl or cycloalkyl, an unsaturated hydrocarbon group such as vinyl or alkenyl, or a silicon-containing hydrocarbon group such as alkylsilyl. Specific examples of $R^1$ include methyl, ethyl, n-propyl, i-propyl, n-butyl, i-butyl, t-butyl, n-amyl, i-amyl, n-hexyl, cyclopropyl, allyl, trimethylsilyl and dimethylethylsilyl groups. Of these groups, alkyl groups having 1 to 4 carbon atoms such as methyl, ethyl, n-propyl, i-propyl, cyclopropyl, n-butyl, i-butyl and t-butyl are preferred.

$R^2$ and $R^3$ are each independently a divalent saturated or unsaturated hydrocarbon group having 3 to 20 carbon atoms. Further, $R^2$ and $R^3$ each satisfy a requirement that at least one of the rings formed therewith be a seven- to twelve-membered ring including two carbon atoms of the cyclopentadiene. From this viewpoint, the chain length of $R^2$ and $R^3$ is such that the ring formed therewith is a multi-membered ring of a ring member of twelve at the biggest.

As described above, the second requirement for $R^2$ and $R^3$ is that at least one, preferably both, of $R^2$ and $R^3$ forms a seven- to twelve-membered ring, preferably a seven- to ten-membered ring. Therefore, $R^2$ and $R^3$ each have 5 to 20 carbon atoms, preferably 5 to 16 carbon atoms, wherein the surplus of carbon atoms over the carbon atoms required for the seven- to twelve-membered ring form a substituent or substituents on the multi-membered ring in question.

The third requirement for $R^2$ and $R^3$ is that when at least one of $R^2$ and $R^3$ forms a condensed ring which is a seven- to twelve-membered ring, the resultant condensed ring has at least one unsaturated bond inherent in $R^2$ or $R^3$ used.

Specific examples of such $R^2$ and $R^3$ are as follows.

(1) Divalent saturated hydrocarbon groups, for example, an alkylene and a cycloalkylene, specifically n-butylene, 1-methylbutylene, 2-methylbutylene, 1,2-dimethylbutylene, 1-cyclopropylbutylene and 1-phenylbutylene; and (2) divalent unsaturated hydrocarbon groups, for example, an alkylene, an alkadienylene and an arylene, specifically 1,3-butadienylene, 2-methyl-1,3-butadienylene, 2-phenyl-1,3-butadienylene, 1-pentenylene, 1,3-pentadienylene, 1,4-pentadienylene, 3-methyl-1,4-pentadienylene, 1,3-hexadienylene, 5-methyl-1,3-hexadienylene, 3,4-dimethyl-1,5-hexadienylene, 1,3,5-hexatrienylene, 1,2-dimethyl-1,3,5-hexatrienylene and 1,3,5-heptatrienylene.

Of these groups, 1,3-pentadienylene, 1,3-hexadienylene, 5-methyl-1,3-hexadienylene, 1,3,5-hexatrienylene, 1,3,5-heptatrienylene, 1,4-pentadienylene, 3-methyl-1,4-pentadienylene and 1,2-dimethyl-1,3,5-hexatrienylene are preferred.

In passing, when $R^2$ is 1,3-pentadienylene, the ligand moiety of the compound of formula [I] is azulene or, in other words, 4-hydro-cyclopentacycloheptene.

Q is a divalent group or a bridge which crosslinks the two conjugated five-membered cyclic ligands, and examples thereof include (i) a divalent hydrocarbon group having 1 to 20 carbon atoms, preferably 1 to 6 carbon atoms, more specifically, for example, a saturated hydrocarbon group such as an alkylene, cycloalkylene, arylene group, (ii) a silylene group, (iii) a silylene group with a hydrocarbyl substituent thereon having 1 to 20 carbon atoms, preferably 1 to 12 carbon atoms, (iv) a germylene group, or (v) a germylene group with a hydrocarbyl substituent thereon having 1 to 20 carbon atoms, preferably 1 to 12 carbon atoms. Of these groups, alkylene, cycloalkylene, arylene and alkylsilylene groups are preferred. The bond-to-bond distance or the "span of bridge" of the divalent Q group is, irrespective of the total number of carbon atoms contained therein, such that when Q is in a chain form, it is preferably about 4 or less atoms, especially 3 or less atoms, while when Q has a cyclic group, it is preferably the cyclic group+about two atoms or shorter, especially the cyclic group alone. Therefore, when Q is an alkylene, the alkylene is preferably ethylene and isopropylidene, wherein the bond-to-bond distance is of two atoms and one atom, respectively; when Q is a cycloalkylene, the cycloalkylene is preferably cyclohexylene, wherein the bond-to-bond distance is one cyclic group, i.e., the cyclohexylene group alone; and when Q is an alkylsilylene, the alkylsilylene is preferably dimethylsilylene, wherein the bond-to-bond distance is one atom, namely a silicon atom.

X and Y each independently, i.e., which may be the same or different, represent (i) a hydrogen atom, (ii) a halogen atom, e.g., a fluorine, chloride, bromine or iodine atom, preferably a chlorine atom, (iii) a hydrocarbon group having 1 to 20 carbon atoms or (iv) a hydrocarbon group having 1 to 20 carbon atoms and containing an oxygen atom, preferably an alkoxy group having 1 to 10 carbon atoms, a nitrogen atom, preferably an amino group having 1 to 12 carbon atoms, a silicon atom, preferably a siloxy group having 1 to 18 carbon atoms or a phosphorus atom, preferably a phosphine group having 1 to 12 carbon atoms.

M is a Group IVB to VIB transition metal of the Periodic Table, preferably a group IVB transition metal, i.e., titanium, zirconium or hafnium, still preferably zirconium.

The compound [I] of the present invention can be synthesized by any method suitable for forming any substituent or bond desired of the compound. One representative synthesis route is as follows. In the following scheme, $HR^a$ represents a compound represented by the following formula:

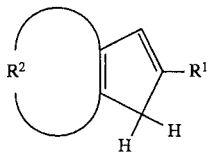

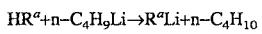

$HR^a + n\text{-}C_4H_9Li \rightarrow R^aLi + n\text{-}C_4H_{10}$ $2R^aLi + QCl_2 \rightarrow Q(R^a)_2 + 2LiCl$ $Q(R^a)_2 + 2.\,n\text{-}C_4H_9Li \rightarrow (R^bLi)_2 + 2.n\text{-}C_4H_{10}$ (wherein $HR^b = R^a$)

$Q(R^bLi)_2 + ZrCl_4 \rightarrow Q(R^b)_2ZrCl_2 + 2LiCl$

Nonlimitative examples of the above-described transition metal compound are as follows. It is to be noted that although the compounds listed below are described simply by their chemical names, they are, as a matter of course, asymmetric in stereostructure as defined previously.

(1) ethylenebis(4,4-dihydroazulenyl)zirconium dichloride, (2) ethylenebis(4-methyl-4-hydroazulenyl)zirconium dichloride, (3) ethylenebis(4,4-dimethylazulenyl)zirconium dichloride, (4) ethylenebis(6-methyl-6-hydroazulenyl)zirconium dichloride, (5) ethylenebis(4-methylazulenyl)zirconium dichloride, (6) ethylenebis(2,4-dimethyl-4-hydroazulenyl)zirconium dichloride, (7) ethylenebis(bicyclo[6.3.0]undeca-pentaenyl)zirconium dichloride, (8) ethylenebis(bicyclo[6.3.0]-2-methyl-undeca-pentaenyl)zirconium dichloride, (9) ethylenebis(bicyclo[6.3.0]-2,4-dimethyl-undecapentaenyl)zirconium dichloride,

(10) ethylenebis(bicyclo[6.3.0]-2-methyl-4-trimethyl-undeca-pentaenyl)zirconium dichloride,

(11) ethylenebis(bicyclo[8.3.0]-trideca-hexaenyl)zirconium dichloride,

(12) ethylenebis(bicyclo[8.3.0]-2-methyl-trideca-hexaenyl)zirconium dichloride,

(13) ethylenebis(bicyclo[8.3.0]-2,4-dimethyl-tridecahexaenyl)zirconium dichloride,

(14) ethylenebis(bicyclo[8.3.0]-2,4,5-trimethyl-tridecahexaenyl)zirconium dichloride,

(15) methylenebis(4-methyl-4-hydroazulenyl)zirconium dichloride,

(16) methylenebis(2,4-dimethyl-4-hydroazulenyl)zirconium dichloride,

(17) isopropylidenebis(4-methyl-4-hydroazulenyl)zirconium dichloride,

(18) cyclohexylidenebis(4-methyl-4-hydroazulenyl)zirconium dichloride,

(19) ethylene( 4-methyl-4-hydroazulenyl) (indenyl) zirconium dichloride,

(20) ethylene( 2,4-dimethyl-4-hydroazulenyl) (2-methylindenyl)zirconium dichloride,

(21) ethylene(4-methyl-4-hydroazulenyl) (4,5,6,7-tetrahydroindenyl)zirconium dichloride,

(22) dimethylsilylenebis(4,4-dihydroazulenyl)zirconium dichloride,

(23) dimethylsilylenebis(4-methyl-4-hydroazulenyl)zirconium dichloride,

(24) dimethylsilylenebis(2,4-dimethyl-4-hydroazulenyl)zirconium dichloride,

(25) dimethylsilylenebis(2,4-dimethylazulenyl)zirconium dichloride,

(26) dimethylsilylenebis(2,6-dimethyl-6-hydroazulenyl)zirconium dichloride,

(27) dimethylsilylenebis(6-methyl-6-hydroazulenyl)zirconium dichloride,

(28) dimethylsilylenebis(bicyclo[6.3.0]undeca-pentaenyl)zirconium dichloride,

(29) dimethylsilylenebis(bicyclo[6.3.0]-2-methylundecapentaenyl)zirconium dichloride,

(30) dimethylsilylenebis(bicyclo[6.3.0]-2,4-dimethyl-undeca-pentaenyl)zirconium dichloride,

(31) dimethylsilylenebis(bicyclo[8.3.0]-trideca-hexaenyl)zirconium dichloride,

(32) dimethylsilylenebis(bicyclo[8.3.0]-2-methyltridecahexaenyl)zirconium dichloride,

(33) dimethylsilylenebis(bicyclo[6.3.0]-2,4-dimethyltridecahexaenyl)zirconium dichloride,

(34) phenylmethylsilylenebis(4-metnyl-4-hydroazulenyl)zirconium dichloride,

(35) phenylmethylsilylenebis(2,4-dimethyl-4-hydroazulenyl)zirconium dichloride,

(36) diphenylsilylenebis(2,4-dimethyl-4-hydroazulene)zirconium dichloride,

(37) diphenylsilylenebis(bicyclo[6.3.0]-2-methyl-undeca-pentaenyl)zirconium dichloride,

(38) dimethylsilylene(4-methyl-4-hydroazulenyl) (indenyl)zirconium dichloride,

(39) dimethylsilylene(2,4-dimethyl-4-hydroazulenyl)(2-methylindenyl)zirconium dichloride,

(40) dimethylsilylene(2,4-dimethyl-4-hydroazulenyl)(2-methyl- 4,5,6,7-tetrahydroindenyl)zirconium dichloride, and

(41) dimethylgermanebis(4-methyl-4-hydroazulenyl)zirconium dichloride.

Further examples of the transition-metal compound include compounds wherein one or both of the chlorides of the above-described compounds are replaced with a bromine, iodine, or hydrogen atom, or a methyl, phenyl, or benzyl group, or an alkoxy group. Still further examples of the transition-metal compound include compounds wherein the zirconium atom of the above-described compounds is replaced with a titanium, hafnium, tantalum, niobium, vanadium, tungsten, or molybdenum atom. Of these compounds, compounds of the Group IVB transition metals, i.e., titanium, zirconium and hafnium, are preferred. Still preferred compounds are those wherein M is zirconium. Particularly preferred are compounds having as a ligand an azulenyl group with a substituent at the 2- and 4-positions, a [6.3.0] undeca-pentaenyl group or an [8.3.0]trideca-hexaenyl group.

<Component (B)>

Component (B) is (i) an aluminum oxy compound, (ii) a Lewis acid or (iii) an ionic compound which can react with Component (A) to convert Component (A) to a cation.

Some Lewis acids can also be regarded as an "ionic compound which can react with Component (A) to convert Component (A) to a cation". Therefore, compounds belonging to both the "Lewis acid" and the "ionic compound which can react with Component (A) to convert Component (A) to a cation" are interpreted as those belonging to any one of these groups.

Specific examples of the aluminum oxy compound include compounds represented by the following general formulae [II], [III] and [IV]:

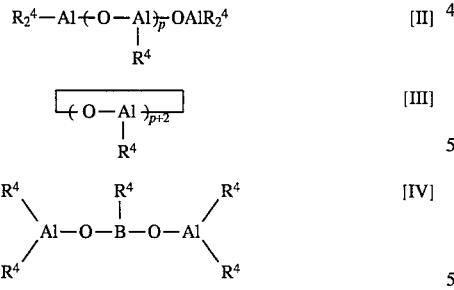

wherein p is a number of 0 to 40, preferably 2 to 30, $R^4$ is hydrogen, a hydrocarbon group or a halogen-containing hydrocarbon group, preferably a hydrocarbon group having 1 to 10 carbon atoms or a halogen-containing hydrocarbon group having 1 to 10 carbon atoms, particularly preferably 1 to 6 carbon atoms.

The compounds represented by the general formulae [II] and [III] are called "alumoxane" that is a product of a reaction of one species of a trialkylaluminum or two or more species of a trialkylaluminums with water. Specific examples of the alumoxanes include (i) alumoxanes obtained from one species of a trialkylaluminum and water, that is, methylalumoxane, ethylalumoxane, propylalumoxane, butylalumoxane and isobutylalumoxane and (ii) alumoxanes obtained from two species of a trialkylaluminum and water, that is, methylethylalumoxane, methylbutylalumoxane, methylisobutylalumoxane, etc. Of these compounds, methylalumoxane and methylisobutylalumoxane are particularly preferred.

It is also possible to use a plurality of alumoxanes selected within and/or between the above groups (i) and (ii). Moreover, the above alumoxanes can be used in combination with another alkylaluminum compound such as trimethylaluminum, triethylaluminum, triisobutylaluminum or dimethylaluminum chloride.

The above alumoxanes can be prepared under the various known conditions. Specifically, the following methods may be mentioned:

(a) the method in which a trialkylaluminum is directly reacted with water in an appropriate organic solvent such as toluene, benzene or ether;

(b) the method in which a trialkylaluminum is reacted with a salt hydrate containing water of crystallization, such as a hydrate of copper sulfate or of aluminum sulfate;

(c) the method in which a trialkylaluminum is reacted with water having impregnated silica gel or the like;

(d) the method in which trimethylaluminum and triisobutylaluminum are mixed and the mixture is directly reacted with water in an appropriate organic solvent such as toluene, benzene, or ether;

(e) the method in which trimethylaluminum and triisobutylaluminum are mixed, and the mixture is reacted, while heating, with a salt hydrate containing water of crystallization, such as a hydrate of copper sulfate or of aluminum sulfate;

(f) the method in which silica gel or the like that has been impregnated with water in advance is treated with triisobutylaluminum, and then subjected to an additional treatment with trimethylaluminum;

(g) the method in which methylalumoxane and isobutylalumoxane are synthesized separately by the known methods, mixed in the predetermined amounts, and reacted with each other while heating; and (h) the method in which a salt containing water of crystallization such as $CuSO_4.5H_2O$ is added to an aromatic hydrocarbon solvent such as benzene or toluene, and reacted with trimethylaluminum at a temperature of approximately −40° C. to 40° C. The amount of water used in these methods, in general, is from 0.5 to 1.5 when expressed by the molar ratio to the trimethylaluminum. The methylalumoxane thus obtained is a linear [II] or cyclic [III] organoaluminum polymer.

The compound represented by the general formula [IV] can be prepared by a reaction between one species of a trialkylaluminum or two or more species of a trialkylaluminums and an alkylboronic acid:

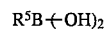

wherein $R^5$ represents an alkyl group having 1 to 10 carbon atoms, preferably 1 to 6 carbon atoms, in a molar ratio of 10:1 to 1:1. Specific examples of the compound include (i) a product of a reaction between trimethylaluminum and methylboronic acid in a ratio of 2:1, (ii) a product of a reaction between triisobutylaluminum and methylboronic acid in a ratio of 2:1, (iii) a product of a reaction among trimethylaluminum, triisobutylaluminum and methylboronic acid in a ratio of 1:1:1, (iv) a product of a reaction between trimethylaluminum and ethylboronic acid in a ratio of 2:1 and (v) a product of a reaction between triethylaluminum and butylboronic acid in a ratio of 2:1. These compounds represented by the general formula [IV] may be used in combination of two or more thereof. Further, it is also possible to use the compounds represented by the general formula [IV] in combination with an alumoxane represented by the general formula [II] or [III] and/or in combination with another alkylaluminum compound such as trimethylaluminum, triethylaluminum, triisobutylaluminum or dimethylaluminum chloride.

Examples of the ionic compound reactive with Component (A) to convert Component (A) to a cation include those represented by the general formula [V]:

$$[K]^{e+}[Z]^{e-} \qquad \text{[V]}$$

wherein K represents an ionic cation component, and examples thereof include carbonium, tropylium, ammonium, oxonium, sulfonium and phosphonium cations. Further examples of the ionic compound include cations of metals and cations of organometals that, as such, are likely to be reduced. Specific examples of these cations include (i) triphenylcarbonium, and diphenylcarbonium, (ii) cycloheptatrienium, and indenium, (iii) triethylammonium, tripropylammonium, tributylammonium, N,N-dimethylanilinium, dipropylammonium, dicyclohexylammonium, (iv) triphenylphosphonium, trimethylphosphonium, tri(dimethylphenyl)phosphonium, and tri(methylphenyl)phosphonium, (v) triphenylsulfonium, (vi) triphenyloxonium, and triethyloxonium, (vii) pyrylium and (viii) a silver ion, a gold ion, a platinum ion, a copper ion, a palladium ion, a mercury ion and a ferrocenium ion.

In the general formula [V], Z is an ionic anion component that is a counter anion (generally in a noncoordination form) against a cation species formed by conversion of Component (A), and examples thereof include organoboron compound anions, organoaluminum compound anions, organogallium compound anions, organophosphorus compound anions, organoarsenic compound anions and organoantimony compound anions.

Specific examples of Z include:

(i) tetraphenylboron, tetrakis(3,4,5-trifluorophenyl)boron, tetrakis(3,5-di(trifluoromethyl)phenyl)boron and tetrakis(3,5-di(t-butyl)phenyl)boron and tetrakis(pentafluorophenyl)boron;

(ii) tetraphenylaluminum, tetrakis(3,4,5-trifluorophenyl)aluminum, tetrakis(3,5-di(trifluoromethyl)phenyl)aluminum, tetrakis(3,5-di(t-butyl)phenyl)aluminum and tetrakis(pentafluorophenyl)aluminum;

(iii) tetraphenylgallium, tetrakis(3,4,5-trifluorophenyl)gallium, tetrakis(3,5-di(trifluoromethyl)phenyl)gallium, tetrakis(3,5-di(t-butyl)phenyl)gallium and tetrakis(pentafluorophenyl)gallium;

(iv) tetraphenylphosphorus and tetrakis(pentafluorophenyl)phosphorus;

(v) tetraphenylarsenic and tetrakis(pentafluorophenyl)arsenic;

(vi) tetraphenylantimony, and tetrakis(pentafluorophenyl)antimony;

(vii) decaborate, undecaborate, carbadodecaborate and decachlorodecaborate.

Examples of the Lewis acid, particularly Lewis acid which can convert Component (A) to a cation, include various organoboron compounds, metal halogen compounds and solid acids. Specific examples thereof include (i) organoboron compounds such as triphenylboron, tris (3,5-difluorophenyl)boron and tris(pentafluorophenyl)boron, (ii) metal halogen compounds such as aluminum chloride, aluminum bromide, aluminum iodide, magnesium chloride, magnesium bromide, magnesium iodide, magnesium chlorobromide, magnesium chloroiodide, magnesium bromoiodide, magnesium chloride hydride, magnesium chloride hydroxide, magnesium bromide hydroxide, magnesium chloride alkoxide and magnesium bromide alkoxide, and (iii) solid acids such as silica-alumina and alumina.

The ionic compound and the Lewis acid may be used as Component (B) alone or in combination therewith or with an aluminum oxy compound represented by the general formula [II], [III] and [IV]. Further, it is also possible to use the ionic compound and the Lewis acid in combination with an organoaluminum compound such as a tri-lower-alkylaluminum, a di-lower-alkylaluminum monohalide, a mono-lower-alkylaluminum dihalide and a lower-alkylaluminum sesquihalide and derivatives of the above-described compounds such that a part of the lower alkyl group has been substituted with a phenoxy group or a halogen atom, for example, trimethylaluminum, triethylaluminum, triisobutylaluminum, diethylaluminum phenoxide and dimethylaluminum chloride.

<Preparation of Catalyst>

The catalyst according to the present invention can be prepared by bringing the above-described Component (A) and Component (B) into contact with each other in the presence or absence of a monomer to be polymerized, inside or outside a polymerization vessel.

The amounts of Components (A) and (B) used in the present invention are not particularly limited. For example, in the case of solvent polymerization, the amount of Component (A) is preferably in the range of from $10^{-7}$ to $10^2$ mmol/liter, still preferably in the range of from $10^{-4}$ to 1 mmol/liter, in terms of the transition metal atom. When use is made of an aluminum oxy compound, the Al/transition metal molar ratio is preferably no lower than 10 and no higher than 100,000, still preferably no lower than 100 and no higher than 20,000, particularly preferably no lower than 100 and no higher than 10,000. When an ionic compound or a Lewis acid is used as Component (B), it is used in an amount in the range of from 0.1 to 1,000, preferably in the range of from 0.5 to 100, still preferably in the range of from 1 to 50, in terms of the molar ratio thereof to the transition metal.

As described above, the catalyst according to the present invention can contain some further component in addition to Components (A) and (B). Examples of the third or optional component which can be added to Components (A) and (B) include compounds containing active hydrogen such as $H_2O$, or an alkanol such as methanol, ethanol and butanol, electron-donating compounds such as ethers, esters and amines, alkoxyl-containing compounds such as phenyl borate, dimethylmethoxyaluminum, phenyl phosphate, tetraethoxysilane and diphenyldimethoxysilane.

When the above catalyst systems are used for the polymerization of olefins, Component (A) and Component (B) may be introduced separately into a reaction vessel or alternatively introduced into a reaction vessel after they are brought into contact with' each other. When Components (A) and Component (B) are previously brought into contact with each other, the contact can be effected in the presence of a monomer to be polymerized, thereby polymerizing part of the olefin, i.e., effecting a so-called "preliminary polymerization".

<Use of Catalyst/Polymerization of Olefin>

The catalyst of the present invention is, of course, applicable to slurry polymerization where a solvent is used and also to polymerizations where substantially no solvent is used such as liquid-phase, non-solvent polymerization, gas-phase polymerization and solution polymerization. Moreover, the catalyst of the invention can also be applied to continuous polymerization and batch-wise polymerization.

In the case of solvent polymerization, a saturated aliphatic and aromatic hydrocarbon such as hexane, heptane, pentane, cyclohexane, benzene and toluene is used as a solvent. They may be used alone or in combination of two or more thereof.

The polymerization temperature is approximately in the range of from −78° to 200° C., preferably in the range of from −20° to 100° C. There is no particular limitation on the olefin pressure of the reaction system. However, the pressure is preferably in the range of from atmospheric pressure to 50 $kg/cm^2 \cdot G$.

In the polymerization, the molecular weight of the polymer can be controlled by any known method, for instance, by properly selecting the temperature or pressure of the polymerization, or by the introduction of hydrogen.

The α-olefins polymerizable in the presence of the catalyst of the present invention, that is, α-olefins (including ethylene) usable for the polymerization reaction in the process according to the present invention are α-olefins having 2 to 20 carbon atoms, preferably 2 to 10 carbon atoms. Specifically, the catalyst of the present invention is preferably used for the stereoregular polymerization of α-olefins having 3 to 10 carbon atoms such propylene, 1-butene, 4-methyl-1-pentene, 1-hexene, 1-octene, 1-decene, 1-dodecene, 1-tetradecene, 1-hexadecene, 1-octadecene and 1-eicosene, particularly preferably for the polymerization of propylene. A mixture of two or more of these α-olefins can also be used for the polymerization.

The catalyst of the present invention can also be used for the copolymerization of the above-described α-olefins of 3 or more carbon atoms with ethylene. Moreover, the catalyst of the present invention is also useful for the copolymerization of the above α-olefins and other monomers copolymerizable therewith, for example, conjugated and non-conjugated dienes such as butadiene, 1,4-hexadiene, 7-methyl-1,6-octadiene, 1,8-nonadiene and 1,9-decadiene, and various cyclic olefins such as cyclopropene, cyclobutene, cyclopentene, norbornene and dicyclopentadiene.

Following examples illustrate the present invention more specifically but non-limitatively.

[Example 1]

Synthesis of Dimethylsilylenebis(4-Methyl-4-Hydroazulenyl)Zirconium Dichloride 150 ml of toluene, which had been dehydrated and purified with Na/K amalgam and 5 g of azulene (39 mmol) were placed in a 500-ml glass flask purged with nitrogen. After the mixture was cooled to no higher than −50° C., 40.0 ml (44 mmol) of a solution of methyllithium (1.10 mol/liter) diluted with diethylether was added dropwise to the mixture over a period of 15 min. After the completion of the addition, the temperature of the reaction system was raised to 50° C. over a period of one hr, and a reaction was allowed to proceed at 50° C. for 2 hr. After the completion of the reaction, the reaction system was cooled to no higher than −50° C. again, and a solution of 2.65 ml (22 mmol) of dimethyldichlorosilane diluted with 10 ml of toluene was added dropwise over a period of 30 min. After the completion of the addition, the temperature of the reaction system was raised to room temperature over a period of one hr. Then, a reaction was allowed to proceed at room temperature for 2 hr and then under reflux of toluene for 10 hr. After the completion of the reaction, the reaction mixture was decomposed with water, and the organic layer was evaporated to dryness. Thereafter, 20 ml of toluene was added to the residue for recrystallization. Thus, 1.2 g of bis(4-methyl-4-hydroazulene)dimethylsilane (Compound (1)) was obtained.

1.0 g (2.9 mmol) of Compound (1) was dissolved in 50 ml of dehydrated THF, and the solution was cooled to no higher than −50° C. Then, 3.7 ml (5.92 mmol) of a solution of n-butyllithium (1.6 mol/liter) diluted with hexane was added thereto. The temperature of the reaction system was raised to room temperature over a period of one hr, and a reaction was allowed to proceed at room temperature for an additional 2 hr. Separately, 50 ml of THF was placed in a 300-ml flask purged with nitrogen and cooled to −60° C. Thereafter, 0.675 g (2.9 mmol) of zirconium tetrachloride was added thereto. The temperature of the mixture was raised to room temperature over a period of one hr, and zirconium tetrachloride was dissolved therein. Then, the temperature of the solution was lowered to no higher than −50° C. again, and a lithium salt of Compound (1) synthesized above was added at a time to the cooled solution. After the completion of the addition, a reaction was allowed to proceed at −50° C. for 4 hr, and the temperature of the reaction system was then raised to room temperature over a period of one hr. Further, the temperature of the reaction system was raised to 60° C., and reaction was allowed to proceed at that temperature for 2 hr. After the completion of the reaction, the reaction mixture was evaporated to dryness by removing the solvent in vacuo. The residue was subjected to extraction with 50 ml of pentane, and the extract was concentrated to about 20 ml which was then allowed to stand in a refrigerator for 2 days. The precipitated crystal was collected by filtration, washed twice with pentane and then dried to give 0.25 g of an intended product (Component (A)-1).

Polymerization of Propylene

A 1.5-liter agitation-type autoclave was thoroughly purged with propylene. 500 ml of toluene which had been thoroughly dehydrated and deoxygenated was introduced into the autoclave. To the toluene were added 3 mmol (0.174 g) (in terms of Al atom) of methylalumoxane (degree of polymerization: 16) manufactured by Toso-Akzo and 0.504 mg (1 μmol) of the dimethylsilylenebis(4-methyl- 4-hydroazulenyl)zirconium dichloride of Component (A)-1 synthesized above. After propylene was introduced into the mixture, preliminary polymerization was carried out at 20° C. and 1 $kg/cm^2 \cdot G$ for 15 min. The temperature of the reaction system was raised to 40° C., and polymerization was carried out at that temperature and 7 $kg/cm^2 \cdot G$ for 2 hr. After the completion of the polymerization, the resultant polymer slurry was filtered to collect a polymer which was then dried to give 102 g of a polymer product. The filtrate was concentrated to give 1.2 g of a polymer. The catalytic activity was $20.5 \times 10^4$ g polymer/g Component (A), and the polymer had a number average molecular weight (Mn) of $6.75 \times 10^4$, a molecular weight distribution (Mw/Mn) of 2.25 and a melting point of 156.5° C.

[Example 2]

Polymerization of Propylene

Propylene was polymerized as in Example 1, except that the polymerization temperature was 70° C. The results are given in Table 1.

[Example 3]

Polymerization of Propylene

Propylene was polymerized as in Example 1, except that 500 ml of toluene, 139 mg (0.7 mmol) of triisobutylaluminum instead of 3 mmol of methylalumoxane and 0.504 mg (1 μmol) of dimethylsilylenebis(4-methyl-4-hydroazulenyl)zirconium dichloride were introduced and use was made of 1.6 mg (2 μmol) of dimethylanilinium[ tetrakis(pentafluorophenyl)borate].

The results are given in Table 1.

[Comparative Example 1]

Synthesis of Dimethylsilylenebis(4,5,6,7-Tetrahydroindenyl)Zirconium Dichloride

Dimethylsilylenebis(tetrahydroindenyl)zirconium dichloride was synthesized according to a method described in J. Orgmet. Chem. (342) 21–29 (1988) and J. Orgmet. Chem. (369) 359–370 (1989).

Specifically, a solution of 5.4 g of bis(indenyl)dimethylsilane diluted with 150 ml of tetrahydrofuran was introduced in 300-ml flask purged with nitrogen and cooled to no higher than −50° C., and 23.6 ml of n-butyllithium (1.6M/liter) was added dropwise over a period of 30 min. After the completion of the dropwise addition, the temperature of the mixture was raised to room temperature over a period of one hr, and a reaction was allowed to proceed at room temperature for 4 hr, thereby synthesizing a reaction mixture A.

200 ml of tetrahydrofuran was introduced into a 500-ml flask purged with nitrogen and cooled to no higher than −50° C., and 4.38 g of zirconium tetrachloride was gradually introduced thereinto. Then, the reaction mixture A was introduced at a time, and the temperature of the mixture was gradually raised to room temperature over a period of 3 hr. A reaction was allowed to proceed at room temperature for 2 hr. The temperature was raised to 60° C., and a reaction was allowed to proceed at that temperature for an additional 2 hr. After the completion of the reaction, the solvent was removed by distillation under reduced pressure. The residue was dissolved in 100 ml of toluene, and the solvent was again removed by distillation to give 3.86 g of a crude crystal of dimethylsilylenebis(indenyl)zirconium dichloride.

Then, the crude crystal was dissolved in 150 ml of dichloromethane, and the solution was introduced into a 500-ml autoclave. After 5 g of platinum-carbon (0.5% by weight platinum supported) catalyst was introduced, a hydrogenation reaction was effected under conditions of $H_2$=50 kg/cm$^2$.G and 50° C. for 5 hr. After the completion of the reaction, the catalyst was removed by filtration, the solvent was removed by distillation under reduced pressure, and the residue was extracted with toluene and then recrystallized to give 1.26 g of dimethylsilylenebis(tetrahydroindenyl)zirconium dichloride as an intended product.

Polymerization of Propylene

Propylene was polymerized as in Example 1, except that Component (A) was used in an amount of 0.456 mg (1 μmol). The results are given in Table 1.

[Comparative Example 2]

Propylene was polymerized as in Comparative Example 1, except that the polymerization temperature was 70° C. The results are given in Table 1.

[Example 4]

Synthesis of Dimethylsilylenebis(2,4-Dimethyl-4-Hydroazulenyl)Zirconium Dichloride 2-Methylazulene was synthesized according to a method described in Japanese Patent Laid-Open Publication No. 207232/1987. Specifically, 19.5 g (0.16 mol) of tropolone was reacted with 40 g (0.21 mol) of p-toluenesulfonic acid chloride in pyridine to give 37.1 g of tosylated tropolone. Then, 20 g (0.15 mol) of dimethylmalonate was reacted with 9.7 g (0.18 mol) of NaOMe in methanol at room temperature for 4 hr to give 14.4 g of 3-methoxycarbonyl-2H-cyclohepta(b) furan-2-one (Compound (2)). Then, 12 g of Compound (2), 200 ml of acetone and 70 ml of diethylamine were added, and the mixture was heated under reflux for 30 hr. Thereafter, $H_2O$ was added thereto, and the mixture was extracted with toluene to give 39.2 g of methyl-2-methylazulene carboxylate. Further, 25 ml of phosphoric acid was added, and a reaction was allowed to proceed at 85° to 90° C. for one hr. The reaction mixture was decomposed with water, extracted with benzene and dried to give 6.5 g of 2-methylazulene as an intended product.

Thereafter, the procedure of Example 1 was repeated to give 0.73 g of dimethylsilylenebis(2,4-dimethyl-4-hydroazulenyl)zirconium dichloride (Component (A)-2).

Polymerization of Propylene

Propylene was polymerized as in Example 1, except that use was made of 0.532 mg (1 μmol) of Component (A)-2. The results are given in Table 1.

[Examples 5 and 6]

Propylene was polymerized as in Examples 2 and 3, except that 0.532 mg of Component (A)-2 synthesized in Example 4 was used as Component (A). The results are given in Table 1.

TABLE 1

| | Component (A) (Amount) | Organo-aluminum compound (Amount) | Others (Amount) | Polymerization conditions | Catalytic activity (g-polymer/g component (A)) | GPC Mn | Mw/Mn | Melting point (°C.) |
|---|---|---|---|---|---|---|---|---|
| Ex. | | | | | | | | |
| -1 | Dimethylsilylenebis (2,4-dimethyl-4-hydroazulenyl) zirconium dichloride (1 μmol) | Methyl-alumoxane (3 mmol) | — | 40° C. 7K2H | 20.5 × 10$^4$ | 6.75 × 10$^4$ | 2.25 | 156.5° C. |
| -2 | ↓ | ↓ | — | 70° C. 7K2H | 28.3 × 10$^4$ | 4.97 × 10$^4$ | 2.05 | 150.3° C. |
| -3 | ↓ | TIBA *1 (0.7 mmol) | Dimethylaniliniumtetrakis (pentafluorophenyl)borate (2 μmol) | 40° C. 7K2H | 31.6 × 10$^4$ | 4.89 × 10$^4$ | 2.18 | 154.4° C. |
| Comp. Ex. | | | | | | | | |
| -1 | Dimethylsylylenebis (2,4-dimethyl-4- | Methyl-alumoxane | — | ↓ | 16.8 × 10$^4$ | 3.25 × 10$^4$ | 2.10 | 149.8° C. |

TABLE 1-continued

| | Component (A) (Amount) | Organo-aluminum compound (Amount) | Others (Amount) | Polymerization conditions | Catalytic activity (g-polymer/g component (A)) | GPC Mn | Mw/Mn | Melting point (°C.) |
|---|---|---|---|---|---|---|---|---|
| -2 Ex. | hydroazulenyl)zirconium dichloride (1 μmol) ↓ | (3 mmol) ↓ | — | 70° C. 7K2H | $43.3 \times 10^4$ | $0.96 \times 10^4$ | 1.95 | 117.5° C. |
| -4 | Dimethylsylylenebis (2,4-dimethyl-4-hydroazulenyl) zirconium dichloride (1 μmol) | ↓ | — | 40° C. 7K2H | $12.7 \times 10^4$ | $19.6 \times 10^5$ | 2.35 | 158.7° C. |
| -5 | ↓ | ↓ | — | 70° C. 7K2H | $18.1 \times 10^4$ | $15.3 \times 10^5$ | 2.28 | 154.3° C. |
| -6 | ↓ | TIBA (0.7 mmol) | Dimethylaniliniumtetrakis (pentafluorophenyl)borate (2 μmol) | 40° C. 7K2H | $20.8 \times 10^4$ | $16.7 \times 10^5$ | 2.55 | 156.6° C. |

What is claimed is:

1. A catalyst component for use in the polymerization of α-olefins which comprises a compound represented by the following general formula [I]:

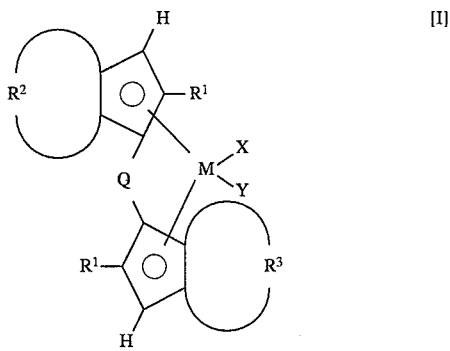

wherein $R^1$s each independently represent a hydrogen atom, a hydrocarbon group having 1 to 6 carbon atoms or a hydrocarbon group having 1 to 12 carbon atoms with a silicon atom contained therein; each of $R^2$ and $R^3$ independently represents a divalent saturated or unsaturated hydrocarbon group having 3 to 20 carbon atoms which forms a ring condensed with the five-membered ring to which it is attached, provided that at least one of $R^2$ and $R^3$ forms the ring condensed which is a seven- to twelve-membered ring having an unsaturated bond inherent in $R^2$ or $R^3$ used; Q represents a divalent hydrocarbon group having 1 to 20 carbon atoms, a silylene group, a silylene group with a hydrocarbon group having 1 to 20 carbon atoms, a germylene group, or a germylene group with a hydrocarbon group having 1 to 20 carbon atoms, which group combines the two five-membered rings with each other; X and Y each independently represent a hydrogen atom, a halogen atom, a hydrocarbon group having 1 to 20 carbon atoms, or a hydrocarbon group having 1 to 20 carbon atoms with an oxygen atom, a nitrogen atom, a silicon atom or a phosphorus atom contained therein; and M represents a Group IVB to VIB transition metal of the Periodic Table.

2. The catalyst component as claimed in claim 1, wherein the metal M in the compound is selected from the group consisting of titanium, zirconium and hafnium.

3. The catalyst component as claimed in claim 2, wherein the metal M is zirconium.

4. The catalyst component as claimed in claim 1, wherein $R^2$ and $R^3$ are each selected from the group consisting of 1,3-pentadienylene, 1,3-hexadienylene, 5-methyl- 1,3-hexadienylene, 1,3,5-hexatrienylene, 1,3,5-heptatrienylene 1,4-pentadienylene, 3-methyl-1,4-pentadienylene and 1,2-dimethyl-1,3,5-hexatrienylene.

5. The catalyst component as claimed in claim 1, wherein $R^1$ is a hydrogen atom.

6. The catalyst component as claimed in claim 1, wherein $R^1$ is an alkyl group of 1 to 4 carbon atoms.

7. The catalyst component as claimed in claim 1, wherein Q is selected from the group consisting of alkylene, cycloalkylene, arylene and alkylsilylene groups.

8. The catalyst component as claimed in claim 1, wherein Q is dimethylsilylene.

* * * * *